United States Patent [19]

Buzzetti et al.

[11] Patent Number: 5,409,949

[45] Date of Patent: Apr. 25, 1995

[54] METHYLEN-OXINDOLE DERIVATIVES COMPOSITIONS AND TYROSINE KINASE INHIBITION THEREWITH

[75] Inventors: Franco Buzzetti, Monza; Antonio Longo, Milan; Maristella Colombo, Cesano Boscone, all of Italy

[73] Assignee: Farmitalia Carlo Erba S.r.l., Milan, Italy

[21] Appl. No.: 987,280

[22] PCT Filed: Jul. 10, 1992

[86] PCT No.: PCT/EP92/01569

§ 371 Date: Mar. 12, 1993

§ 102(e) Date: Mar. 12, 1993

[87] PCT Pub. No.: WO93/01182

PCT Pub. Date: Jan. 21, 1993

[30] Foreign Application Priority Data

Jul. 12, 1991 [GB] United Kingdom ............... 9115160

[51] Int. Cl.$^6$ .................... C07D 401/06; A61K 31/40
[52] U.S. Cl. .................... 514/414; 548/455; 514/421
[58] Field of Search ............. 548/455; 514/414

[56] References Cited

U.S. PATENT DOCUMENTS 4,642,309  2/1987  Michel et al. .

FOREIGN PATENT DOCUMENTS 3310891  9/1984  Germany .
91/13055 9/1991  WIPO .

OTHER PUBLICATIONS

Patent Abstracts of Japan, 19 Sep. 1991, & JP, A, 3 213 847.
Canadian J. Chem. vol. 46, No. 13, 1 Jul. 1968, pp. 2189–2194; R. Hodges, et al.: 'Chemical and biological properties of some oxinodolidyl-3-methines'.
Chem. Ber. vol. 102, No. 4, 1969, pp. 1347–1356; H. Von Dobeneck et al.: 'alpha.beta'-Diindolylmethane und-methene. Der Urorosein-Chromophor'.
Yakugaku Zasshi, vol. 97, No. 9, 1977, pp. 1033–1039; G. Kobayashi et al.: "Anti-tumor Activity of Indole Derivatives".

Primary Examiner—David B. Springer
Attorney, Agent, or Firm—Oblon, Spivak, McClelland, Maier & Neustadt

[57] ABSTRACT

The invention provides new methylen-indole derivatives of formula (I)

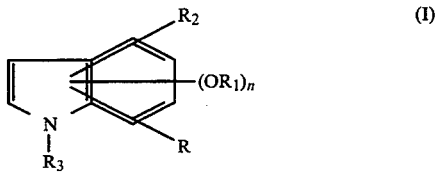

wherein
R is a group

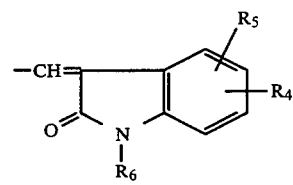

in which
$R_4$ is hydrogen, hydroxy, $C_1$-$C_6$ alkoxy, $C_2$-$C_6$ alkanoyloxy, carboxy, nitro or $NHR_7$, wherein $R_7$ is hydrogen or $C_1$-$C_6$ alkyl;
$R_5$ is hydrogen, $C_1$-$C_6$ alkyl or halogen; and
$R_6$ is hydrogen or $C_1$-$C_6$ alkyl;
n is zero, 1 or 2;
$R_1$ is hydrogen, $C_1$-$C_6$ alkyl or $C_2$-$C_6$ alkanoyl;
$R_2$ is hydrogen, $C_1$-$C_6$ alkyl, halogen, cyano, carboxyl, nitro or $-NHR_7$ in which $R_7$ is as defined above;
$R_3$ is hydrogen, $C_1$-$C_6$ alkyl or $C_2$-$C_6$ alkanoyl; and the pharmaceutically acceptable salts thereof; and wherein, when, at the same time, $R_2$ is hydrogen, $C_1$-$C_6$ alkyl, halogen or cyano and $R_3$ is hydrogen, $R_1$ and n being as defined above, then at least one of $R_4$, $R_5$ and $R_6$ is other than hydrogen, which are useful as tyrosine kinase inhibitors.

7 Claims, No Drawings

METHYLEN-OXINDOLE DERIVATIVES COMPOSITIONS AND TYROSINE KINASE INHIBITION THEREWITH

The present invention relates to new 3-methylene-2-oxindole derivatives, to a process for their preparation, to pharmaceutical compositions containing them and to their use as therapeutic agents.

The present invention provides compounds having the following general formula (I)

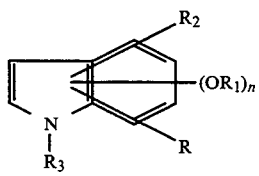

wherein
R is a group

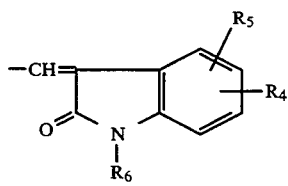

in which
$R_4$ is hydrogen, hydroxy, $C_1$–$C_6$ alkoxy, $C_2$–$C_6$ alkanoyloxy, carboxy, nitro or $NHR_7$, wherein $R_7$ is hydrogen or $C_1$–$C_6$ alkyl;
$R_5$ is hydrogen, $C_1$–$C_6$ alkyl or halogen; and
$R_6$ is hydrogen or $C_1$–$C_6$ alkyl;
n is zero, 1 or 2;
$R_1$ is hydrogen, $C_1$–$C_6$ alkyl or $C_2$–$C_6$ alkanoyl;
$R_2$ is hydrogen, $C_1$–$C_6$ alkyl, halogen, cyano, carboxyl, nitro or —$NHR_7$ in which $R_7$ is as defined above;
$R_3$ is hydrogen, $C_1$–$C_6$ alkyl or $C_2$–$C_6$ alkanoyl; and the pharmaceutically acceptable salts thereof; and wherein, when, at the same time, $R_2$ is hydrogen, $C_1$–$C_6$ alkyl, halogen or cyano and $R_3$ is hydrogen, $R_1$ and n being as defined above, then at least one of $R_4$, $R_5$ and $R_6$ is other than hydrogen. In the compounds of the present invention each of the substituents R, —$OR_1$ and $R_2$ may be independently on either of the benzene or pyrrole moiety of the condensed indole ring system.

The invention includes within its scope all the possible isomers, stereoisomers, in particular Z and E isomers and their mixtures, and the metabolites and the metabolic precursors or bio-precursors (otherwise known as pro-drugs) of the compounds of formula (I).

The substituent R is preferably linked to position 2 or 3 of the indole ring, in particular to position 3.

When n is 2, each of the —$OR_1$ groups may be the same or different.

A substituent —$OR_1$ is preferably linked to position 4, 5, 6 or 7, in particular to position 5 or 7.

The substituent $R_2$ is preferably on the benzene ring moiety, in particular linked to position 5.

Of course only one of the substituents R, —$OR_1$ and $R_2$ can be linked to the same position in the indole ring system. The substituent $R_4$ is preferably linked to position 4 or 5, in particular to position 5.

When $R_4$ is carboxyl, nitro or —$NHR_7$, in which $R_7$ is as defined above, the $R_2$ substituent preferably has not the same meanings. Vice versa, when $R_2$ is carboxyl, nitro or —$NHR_7$, in which $R_7$ is as defined above, the $R_4$ substituent preferably is other than carboxy, nitro or —$NHR_7$.

The alkyl groups, and the alkyl moiety in the alkanoyl groups, may be branched or straight alkyl chain. A $C_1$–$C_6$ alkyl group is preferably a $C_1$–$C_4$ alkyl group, e.g. methyl, ethyl, propyl, isopropyl, butyl, sec-butyl or tert-butyl, in particular methyl or ethyl. A $C_2$–$C_6$ alkanoyl group is preferably a $C_2$–$C_4$ alkanoyl group, in particular acetyl, propionyl or butyryl. A halogen is, preferably, chlorine, bromine or fluorine, in particular bromine.

Pharmaceutically acceptable salts of the compounds of the invention include acid addition salts, with inorganic, e.g. nitric, hydrochloric, hydrobromic, sulphuric, perchloric and phosphoric acids, or organic, e.g. acetic, propionic, glycolic, lactic, oxalic, malonic, malic, maleic, tartaric, citric, benzoic, cinnamic, mandelic and salicylic acids, and salts with inorganic, e.g. alkali metal, especially sodium or potassium, bases or alkaline-earth metal, especially calcium or magnesium bases, or with organic bases, e.g. alkylamines, preferably triethylamine.

As stated above the present invention also includes within its scope pharmaceutically acceptable bio-precursors (otherwise known as pro-drugs) of the compounds of formula (I), i.e. compounds which have a different formula to formula (I) above but which nevertheless upon administration to a human being are converted directly or indirectly in vivo into a compound of formula (I). Preferred compounds of the invention are the compounds of formula (I), wherein
R is as defined above, $R_4$ is hydroxy, amino, nitro or carboxy and $R_5$ and $R_6$ are hydrogen;
$R_1$ is hydrogen or $C_1$–$C_6$ alkyl;
n is zero or 1;
$R_2$ is hydrogen, carboxy, amino or nitro;
$R_3$ is hydrogen; and the pharmaceutically acceptable salts thereof.

More preferred compounds of the invention are the compounds of formula (I) in which
R is as defined above, $R_4$ is hydroxy, amino or carboxy; and $R_5$ and $R_6$ are hydrogen; n is 0 or 1; $R_1$ is hydrogen; $R_2$ is hydrogen, amino or carboxy; $R_3$ is hydrogen; and the pharmaceutically acceptable salts thereof.

Examples of specific compounds of the invention are the following compounds which, when appropriate, may be either Z- or E-diastereomers or Z,E-mixtures of said diastereomers:
5-hydroxy-3-[(3'-indolyl)methylene]-2-oxindole;
3-[(5'-carboxy-3'-indolyl)methylene]-2-oxindole;
3-[(5'-amino-3'-indolyl)methylene]-2-oxindole;
5-carboxy-3-[(3'-indolyl)methylene]-2-oxindole;
5-amino-3-[(3'-indolyl)methylene]-2-oxindole;
5-hydroxy-3-[(5'-hydroxy-3'-indolyl)methylene]-2-oxindole;
5-hydroxy-3-[(7'-hydroxy-3'-indolyl)methylene]-2-oxindole;
3-[(5',7'-dihydroxy-3'-indolyl)methylene]-2-oxindole;
5-amino-3-[(5'-hydroxy-3'-indolyl)methylene]-2-oxindole;

5-hydroxy-3-[(5'-amino-3'-indolyl)methylene]-2-oxindole;

5-carboxy-3-[(5'-hydroxy-3'-indolyl)methylene]-2-oxindole;

5-hydroxy-3-[(5'-carboxy-3'-indolyl)methylene]-2-oxindole;

5-amino-3-[(7'-hydroxy-3'-indolyl)methylene]-2-oxindole;

5-carboxy-3-[(7'-hydroxy-3'-indolyl)methylene]-2-oxindole;

and, if the case, the pharmaceutically acceptable salts thereof.

The compounds of the invention, and the pharmaceutically acceptable salts thereof, can be obtained by a process comprising the condensation of an aldehyde of formula (II)

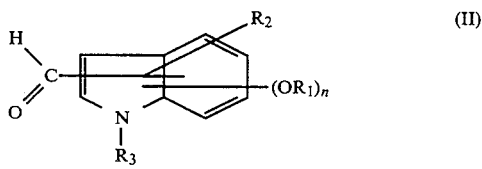

wherein $R_1$, $R_2$, $R_3$ and n are as defined above, with a compound of formula (III)

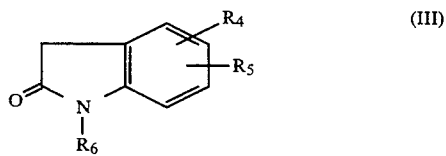

wherein $R_4$, $R_5$ and $R_6$ are as defined above; and, if desired, converting a compound of formula (I) into another compound of formula (I), and/or, if desired, converting a compound of formula (I) into a pharmaceutically acceptable salt thereof, and/or, if desired, converting a salt into a free compound, and/or, if desired, separating a mixture of isomers of a compound of formula (I) into the single isomers. Each of the substituents $R_2$, —$OR_1$ and —CHO in a compound of formula (II) may be independently on either of the benzene or pyrrole moiety of the indole ring.

The reaction of a compound of formula (II) with a compound of formula (III) is an analogy process which can be carried out according to known methods, as herebelow described; preferably in the presence of a basic catalyst, e.g. pyridine, piperidine, dimethylamine, or a suitable alkali metal hydroxide or alkoxide.

For example the reaction of a compound of formula (II) with a compound of formula (III) may be carried out under the conditions of the Knoevenagel reactions as described e.g. by G. Jones in Organic Reactions 15, 204 (1967). Suitable catalyst are organic bases such as pyridine, piperidine or diethylamine. The condensation may be performed in an inert organic solvent e.g. pyridine, ethanol, methanol, benzene or dioxane at temperatures ranging from about 0° C. to about 100° C.

Preferably the reaction is carried out in warm ethanol solution in the presence of piperidine catalyst.

A compound of formula (I) can be converted into another compound of formula (I) according to known methods. For example the de-etherification of a compound of formula (I), wherein one or more $R_1$ substituents are $C_1$-$C_6$ alkyl, so as to obtain a compound of formula (I) wherein one or more $R_1$ substituents are hydrogen may be performed by well known methods in organic chemistry. In the case of a phenolic methyl ether the cleavage can be carried out for example with boron tribromide as described by J. F. N. McOmie in Tetrahedron 24, 2289 (1968). It is advisable to use about 1 mole of boron tribromide for each ether group together with an extra mol of reagent for each group containing a potentially basic nitrogen or oxygen. The reaction may be performed in an inert organic solvent such as methylene chloride, pentane or benzene under an inert, e.g. nitrogen, atmosphere at temperatures ranging from about −78° C. to about room temperature.

The acylation of a compound of formula (I) wherein one or more of —$OR_1$ and/or $R_4$ is hydroxy, so as to obtain a corresponding compound of formula (I) wherein one or more of —$OR_1$ and/or $R_4$ is a $C_2$-$C_6$ alkanoyloxy group, may be obtained by reaction with a reactive derivative of a suitable carboxylic acid, such as an anhydride or halide, in the presence of a basic agent, at temperatures ranging from about 0° C. to about 50° C. Preferably the acylation is carried out by reaction with the respective anhydride in the presence of an organic base, such as pyridine.

The optional salification of a compound of formula (I) as well as the conversion of a salt into the free compound and the separation of a mixture of isomers into the single isomers may be carried out by conventional methods.

For example the separation of a mixture of geometric isomers, e.g. cis- and trans-isomers, may be carried out by fractional crystallization from a suitable solvent or by chromatography, either column chromatography or high pressure liquid chromatography.

The compounds of formula (II) may be obtained according to known methods from compounds of formula (IV)

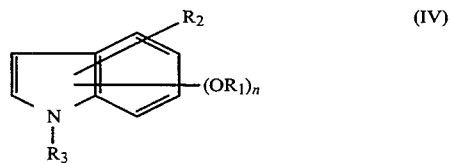

For example the 3-formylindole derivatives of formula (II) can be obtained from a compound (IV) by formylation with N-methylformanilide and phosphorous oxychloride according to the well known Vilsmeyer-Haack method (for a review see W. G. Jackson et al., J. Am. Chem. Soc. 1981, 103, 533). The 2-formylindole derivatives are obtained when the 3-position is occupied.

The compounds of formula (III) and (IV) are known or may be obtained by known methods from known compounds.

PHARMACOLOGY

The compounds of the invention possess specific tyrosine kinase inhibiting activity. Hence they can be useful in the treatment of cancer and other pathological proliferative conditions, such as to inhibit the development of the atheromatous plaque, in mammals, including humans.

Typical therapeutical indications according to the latter use are reocclusion following coronary angioplasty and in general decrease of coronary artery disease.

Recent studies on the molecular basis of neoplastic transformation have identified a family of genes, designed oncogenes, whose aberrant expression causes tumorigenesis.

For example, the RNA tumor viruses possess such an oncogene sequence whose expression determines neoplastic conversion of infected cells. Several of their oncogene-encoded proteins, such as $pp60^{v\text{-}src}$, $p70^{gag\text{-}yes}$, $p130^{gag\text{-}fps}$ and $P70^{gag\text{-}fgr}$ display protein tyrosine kinase activity, that is they catalyse the transfer of the α-phosphate from adenosine triphosphate (ATP) to tyrosine residues in protein substrate. In normal cells, several growth factor receptors, for example the receptors for PDGF, EGF, α-TGF and insulin, display tyrosine kinase activity.

Binding of the growth factor (GF) activates the receptor tyrosine kinase to undergo autophosphorylation and to phosphorylate closely adjacent molecules on tyrosine. Therefore, it is thought that the phosphorylation of these tyrosine kinase receptors plays an important role in signal transduction and that the principal function of tyrosine kinase activity in normal cells is to regulate cell growth. Perturbation of this activity by oncogenic tyrosine kinases that are either overproduced and/or display altered substrate specificity may cause loss of growth control and/or neoplastic transformation. Accordingly, a specific inhibitor of tyrosine kinases can be useful in investigating the mechanism of carcinogenesis, cell proliferation and differentiations and it can be effective in prevention and chemotherapy of cancer and in other pathological proliferative conditions.

The tyrosine specific protein kinase activity of these compounds is shown by the in vitro tests described herebelow.

v-abl kinase purification

The enzyme used in the Abelson tyrosine kinase $p95^{v\text{-}ab}$ which was produced and isolated as follows: 1 Liter cultures of HB-130 cells in LB medium, supplemented with ampicillin, were grown at 30° C. as described by Wang et al. in J. Biol. Chem. 260, 64 (1985). The expression of v-abl protein was induced by shifting the temperature to 42° C. for 3-4 h. The bacterial cells were collected on ice, centrifuged and frozen in liquid nitrogen. The cell pellet was lysed as described by Ferguson et al. in J. Biol. Chem. 260, 3652 (1985) and in Biochem. J. 257, 321 (1989). Briefly, bacterial proteins were removed by differential solubilization with sodium deoxycholate, NaCl and β-octylglucopyranoside in different steps. Insoluble v-abl protein was solubilized with 2M KSCN and dialyzed against 100 volumes of 50 mM Tris-HCl, pH 7.5, 1 mM EDTA and 0.1 mM dithiothreitol (buffer A). The soluble proteins were separated by chromatography on a prepacked Mono-Q anion exchange column in a f.p.l.c. system. The v-abl activity was eluted with a linear KCl gradient (O-I M buffer A). Active fractions were pooled, made 50% in glycerol and stored in small aliquots at −20° C.

Myelin Basic Proteins phophorylation assay

The in vitro test with Myelin Basic Protein as substrate was carried out as follows: Protein phosphorylation was performed by incubating 40 ng of purified v-abl kinase, 1.5 μCi [α-$^{32}$p] ATP, 10 μM cold ATP, 56 μM myelin basic protein in 50 μl of Tris-HCl 25 mM, pH 8.0, containing $MgCl_2$ 10 mM, dithiothreitol 0.1 mM (kinase buffer) at 22° C. The reaction was stopped by addition of equal volumes of 2-fold concentrated Laemmli electrophoresis buffer [U. K. Laemmli, Nature (London) 230, 680 (1970). Samples were boiled again for 3 min and separated in SDS-PAGE (15% acrylamide). Gels were dried and exposed to autoradiographic films for 15-30 min at −70° C. Bands were located by autoradiography, excised from gel and counted in a liquid scintillation counter.

Autophosphorylation assay

For the autophosphorylation assay the v-abl kinase was immunoprecipitated with antiphosphotyrosine antibodies and the resulting immunocomplex analyzed in 50 μl of kinase buffer in the presence of 10 μM ATP and 10 μCi [α-$^{32}$P]-ATP. The reaction was stopped after 15 min at room temperature with boiling Laemmli buffer. Samples were boiled again for 3 min and separated in SDS-PAGE 18% acrylamide). Gels were dried and exposed to autoradiographic films for up to 3 h at −70° C. Bands were located by autoradiography, excised and counted as above. In table I and II a representative compound of this invention is compared with the corresponding non hydroxylated analog which is encompassed by the general formula of patent application WO91/13055. The comparison shows that the introduction of an hydroxyl group, while increasing only slightly the potency toward exogenous substrates significantly enhances the inhibitory activity on the autophosphorylation.

TABLE I

| Myelin Basic Protein phosphorylation assay. | |
|---|---|
| | $IC_{50}$ (μM) |
| 5-hydroxy-3-[(3'-indolyl)methylen]-2-oxindole | 0.4 |
| 3-[(3'-indolyl)methylen]-2-oxindole | 0.6 |

TABLE II

| Autophosphorylation assay. | |
|---|---|
| | $IC_{50}$ (μM) |
| 5-hydroxy-3-[(3'-indolyl)methylen]-2-oxindole | 0.4 |
| 3-[(3'-indolyl)methylen]-2-oxindole | 10 |

In view of their high activity and low toxicity, the compounds of the invention can be used safely in medicine. For example, the approximate acute toxicity ($LD_{50}$) of the compounds of the invention in the mouse, determined by single administration of increasing doses and measured on the seventh day after the treatment was found to be negligible.

The compounds of the invention can be administered in a variety of dosage forms, e.g. orally, in the form of tablets, capsules, sugar or film-coated tablets, liquid solutions or suspensions; rectally, in the form of suppositories; parenterally, e.g. intramuscularly, or by intravenous injection or infusion; or topically. The dosage depends on the age, weight, conditions of the patient and administration route; for example, the dosage adopted for oral administration to adult humans may range from about 10 to about 150–200 mg per dose, from 1 to 5 times daily. Of course, these dosage regimens may be adjusted to provide the optimal therapeutic response.

The invention includes pharmaceutical compositions comprising a compound of formula (I) or a pharmaceutically acceptable salt thereof in association with a pharmaceutically acceptable excipient (which can be a carrier or diluent).

Object of the present invention is also the use of a compound of formula (I), as defined above, or a pharmaceutically acceptable salt thereof, for the manufacture of a medicament for use as tyrosine kinase inhibitor, in particular as anti-cancer and anti-proliferative agent. The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating or film-coating processes.

The liquid dispersion for oral administration may be, e.g., syrups, emulsions and suspensions.

The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol and, if desired, a suitable amount of lidocaine hydrochloride.

The solutions for intravenous injections or infusion may contain as carrier, for example, sterile water or, preferably, they may be in the form of sterile, aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin. Compositions for topical application, e.g. creams, lotions, or pastes, can be prepared by admixing the active ingredient with a conventional oleaginous or emulsifying excipient.

A further object of the present invention is a combined method of treatment of cancer in mammals, including humans, in need of such treatment, said method comprising administering 1) a compound of formula (I), or a pharmaceutically acceptable salt thereof, and
2) an additional antitumor agent, in amounts and close enough together in time sufficient to produce a therapeutically useful effect.

Object of the present invention is also to provide products containing a compound of formula (I), or a pharmaceutically acceptable salt, and an additional antitumor agent as a combined preparation for simultaneous, separate or sequential use in anti-cancer therapy.

The term "antitumor agent" is meant to comprise both a single antitumor drug and "cocktails" i.e. a mixture of such drugs, according to the clinical practice.

Antitumor agents that can be formulated with a compound of the invention or, alternatively, can be administered in a combined method of treatment, are e.g. doxorubicin, daunomycin, epirubicin, idarubicin, etoposide, fluorouracil, mephalan, cyclophosphamide, bleomycin, vinblastin and mitomycin or a mixture of two or more thereof.

The compounds of the invention can therefore be used in a treatment to ameliorate a cancer. They may be administered to a patient suffering from a cancer treatable with an antitumor agent, for example an anthracycline glycoside such as doxorubicin, daunomycin, epirubicin or idarubicin as mentioned above, together with the antiproliferative agent. A compound of the invention and an antitumor agent such as an anthracycline glycoside can be administered to improve the condition of a patient having a leukaemia such as myeloblastic leukaemia, lymphoma, sarcoma, neuroblastoma, Wilm's tumor or malignant neoplasm of the bladder, breast, lung or thyroid.

The following examples illustrate but do not limit the invention.

EXAMPLE 1

5-Hydroxy-3-[(3'-indolyl)methylene]-2-oxindole

[I, R as defined, $n=0$, $R_2=R_3=R_5=R_6=H$, $R_4=5$-OH]

A solution of 3-indolecarboxaldehyde (145 mg, 1 mmol), 5-hydroxy-2-oxindole (149 mg, 1 mmol) and piperidine (60 mg, 0.7 mmol) in absolute ethanol (10 ml) is heated for 3 h at 60° C. under nitrogen. Then the reaction mixture is chilled and evaporated under vacuum to dryness. The residue is submitted to column chromatography over silica gel using methylenechloride/ethanol 4% as eluant. Pure title compound is so obtained in 60% yield (166 mg). Alternatively, the reaction mixture is concentrated under vacuum and then chilled to 0°–5° C., the precipitate filtered, the residue washed with ice-cooled ethanol and finally dried under vacuum. Compounds of higher purity are obtained by further crystallization from ethanol.

$C_{17}H_{12}N_2O_2$ requires: C 73.89 H 4.38 N 10.14 found: C 73.51 H 4.21 N 9.92 MS m/z: 276 IR cm$^{-1}$ (KBr): 3600–2500 (NH, OH), 1650 (CO), 1600, 1580, 1530, 1480 (C=C) m.p. 293° C. (dec.).

According to the above described procedure, the following compounds can be prepared:

5-carboxy-3-[(3'-indolyl)methylene]-2-oxindole;

5-amino-3- [3'-indolyl)methylene]-2-oxindole;

5-hydroxy-3- [(5'hydroxy-3'-indolyl)methylene]-2-oxindole;

MS m/z: 282 IR cm$^{-1}$ (KBr): 3600–2600 (NH, OH), 1655 (CO), 1605, 1585, 1535 (C=C)

5-hydroxy-3-[(7'-hydroxy-3'-indolyl)methylene]-2-oxindole;

3-[(5',7'-dihydroxy-3'-indolyl)methylene]-2-oxindole;

5-amino-3-[(5'-hydroxy-3'-indolyl)methylene]-2-oxindole;

5-hydroxy-3-[(5'-amino-3'-indolyl)methylene]-2-oxindole;

5-carboxy-3-[(5'-hydroxy-3'-indolyl)methylene]-2-oxindole;

5-hydroxy-3-[(5'-carboxy-3'-indolyl)methylene]-2-oxindole;

5-amino-3-[(7'-hydroxy-3'-indolyl)methylene]-2-oxindole;

5-carboxy-3-[(7'-hydroxy-3'-indolyl)methylene]-2-oxindole;

5-methoxy-3-[(5'-methoxy-3'-indolyl)-methylene]-2-oxindole;

5-acetoxy-3-[(5'-acetoxy-3'-indolyl)methylene]-2-oxindole;

3-[(5'-carboxy-3'-indolyl)methylene]-2-oxindole,
$C_{18}H_{12}N_2O_3$ requires: C 71.04; H 3.98; N 9.21 found: C 70.83; H 4.6; N 8.85 MS m/z: 304; m.p.>330° dec. IR cm$^{-1}$ (KBr): 3600–3000 (NH), 3000–2100 (OH), 1710 (CO), 1640, 1620, 1600, 1550 (arom);

3-[(5'-amino-3'-indolyl)methylene]-2-oxindole,
$C_{17}H_{13}N_3O$ requires: C 74.14; H 4.71; N 15.26 found: C 73.88; H 4.51; N 14.91 MS m/z 275; m.p. 250° dec. IR cm$^{-1}$ (KBr) : 3300, 2380 (NH), 1670 (CO), 1600, 1510 (C=C);

3-[(5'-nitro-3'-indolyl)methylen]-2-oxindole,
$C_{17}H_{11}N_3O_3$ requires: C 66.88; H 3.63; N 13.76 found: C 66.58; H 3.74; N 13.64 MS m/z 305; m.p.>350° C. IR cm$^{-1}$ (KBR): 3350, 3230 (NH), 1680 (CO), 1620, 1605, 1580 (C=C), 1530, 1340 (NO$_2$);

3- [(1'-methyl-3'-indolyl)methylen]-2-oxindole,
$C_{18}H_{14}N_2O$ requires: C 78.81; H 5.14; N 10.21 found: C 78.42; H 5.17; N 10.00 MS m/z 274 m.p. 230° C. (dec.) IR cm$^{-1}$ (KBr): 3300–2000 (NH), 1680 (CO), 1610, 1600, 1570, 1500 (C=C);

3-[(3'-indolyl)methylen]-1-methyl-2-oxindole,
$C_{18}H_{14}N_2O$ requires: C 78.81; H 5.14; N 10.21 found: C 78.61; H 5.16; N 10.23 MS m/z 274 m.p. 274° C. IR cm$^{-1}$ (KBr): 3220 (NH), 1675 (CO), 1605, 1500, 1490 (C=C).

EXAMPLE 2

5-Hydroxy-3-[(5'-hydroxy-3'-indolyl)methylene]-2-oxindole

[I, R as defined, n=1, $R_1=R_2=R_3=R_5=R_6=H$, $R_4=5$-OH]

The starting material for this de-etherification example is 5-methoxy-3-[(5'-methoxy-3'-indolyl)methylene]-2-oxindole, which can be obtained according to the procedure described in Example 1.

To a stirred solution of 5-methoxy-3-[(5'-methoxy-3'-indolyl) methylene]-2-oxindole (310 mg, 1 mmol) in anhydrous dichloromethane (10 ml) is added at −78° C. under nitrogen, over a period of 10 min, a 1.0M solution of boron tribromide in dichloromethane (3 ml, 3 mmol). The resulting mixture is stirred for another 1 h at −78° C. and then allowed to warm to room temperature. After stirring for 1.5 h at 20°-25° C. the mixture is cooled to −10° C. and then quenched by the dropwise addition of water (10 ml) over a 10-min period. After addition of ethylacetate the organic layer is separated, washed with water, dried with Na$_2$SO$_4$ and evaporated under vacuum to dryness. The residue is crystallized from ethanol thus giving 198 mg of pure title compound (yield 70%).

$C_{17}H_{12}N_2O_3$ requires: C 72.33 H 4.29 N 6.38 found: C 72.11 H 4.07 N 6.29 MS m/z: 282 IR cm$^{-1}$ (KBr): 3600–2600 (NH, OH), 1655 (CO), 1605, 1585, 1535 (C=C)

According to the above described procedure and starting from the corresponding methylether, the hydroxyl compounds mentioned in Example 1 can be obtained.

EXAMPLE 3

5-Acetoxy-3-[(5'-acetoxy-3'-indolyl)methylene]-2-oxindole

[I, R as defined, n=1, $R_1=Ac$, $R_4=5$-OAc, $R_2=R_3=R_5=R_6=H$]

The starting material for this acylation example is 5-hydroxy-3-[(5'-hydroxy-3'-indolyl)methylene]-2-oxindole, which may be obtained according to the procedure described in Examples 1 and 2.

To a cooled solution of 5-hydroxy-3-[(5'-hydroxy-3'-indolyl) methylene]-2-oxindole (282 mg, 1 mmol) in dry pyridine (0.5 ml) is added acetic anhydride (306 mg, 3 mmol) and the mixture maintained at 0°-5° C. overnight. Thereupon the mixture concentrated under vacuum, the residue dissolved in dichloromethane, the organic layer washed with water and then evaporated under reduced pressure. The crude product is crystalized from chloroform/methanol to yield pure title compound in 80% yield (301 mg).

$C_{21}H_{16}N_2O_5$ requires: C 67.02 H 4.29 N 7.44 found: C 66.91 H 4.05 N 7.29 MS m/z: 376 IR cm$^{-1}$ (KBr): 3600–3200 (NH), 1750 (CH$_3$COO), 1650 (CONH), 1600, 1580, 1530 (C=C)

According to the above described procedure, the hydroxyl compounds obtained in Example 1 and 2 can be transformed into the corresponding $C_2$-$C_6$ alkanoyloxy derivatives.

EXAMPLE 4

5-Nitro-3-indolealdehyde. [II, n=0, $R_2=5$-NO$_2$, $R_3=H$]

A mixture of N-methylformanilide (176 mg, 1.3 mmol) and phosphorous oxychloride (199 mg, 1.3 mmol) is stirred for 15 min at 20°-25° C. under nitrogen. then a solution of 5-nitroindole (162 mg, 1 mmol) in 1,2-dichloroethane (5 ml) is added and the mixture heated to reflux for 3 h. After cooling the mixture is poured onto iced water, the precipitate filtered off and washed with water. Thereupon the residue is chromatographed over silica gel using benzene/ethyl acetate as eluant. Thus pure title compound is obtained in 80% yield (152 mg).

$C_9H_6N_2O_3$ requires: C 56.85 H 3.18 N 14.73 found: C 56.79 H 3.01 N 14.51 MS m/z: 190 IR cm$^{-1}$ (KBr): 3140, 3090 (NH), 1650 (CO), 1511, 1345 (NO$_2$)

These nitro-intermediates besides leading to final products of formula (I) with $R_2=NO_2$ give also rise to final products with $R_2=NH_2$ obtainable from the former by reduction. By proceding analogously, the following protected intermediates can be prepared, which after deprotection at a suitable stage of the synthesis give also rise to final product of formula (I) with free carboxyl ($R_2=COOH$) and free hydroxyl ($R_2=OH$) respectively:

3-carbomethoxy-3-indolealdehyde; and 3-methoxy-3-indolealdehyde.

EXAMPLE 5

Tablets each weighing 0.150 g and containing 25 mg of the active substance, can be manufactured as follows: composition (for 10,000 tablets):

| | |
|---|---|
| 5-Hydroxy-3-[(3'-indolyl)methylene]-2-oxindole | 250 g |
| Lactose | 800 g |

| | |
|---|---|
| Corn starch | 415 g |
| Talc powder | 30 g |
| Magnesium stearate | 5 g |

The 5-hydroxy-3-[(3'-indolyl)methylene]-2-oxindole, the lactose and half the corn starch are mixed; the mixture is then forced through a sieve of 0.5 mm mesh size.

Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets.

EXAMPLE 6

Capsules, each dosed at 0.200 g and containing 20 mg of the active substance can be prepared.

Composition for 500 capsules:

| | |
|---|---|
| 3-[(5'-amino-3'-indolyl)methylene]-2-oxindole | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

We claim:

1. A compound of formula (I):

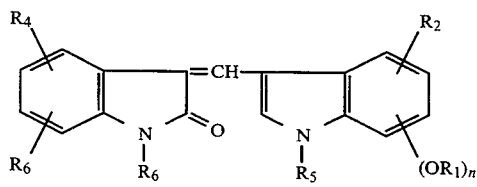

in which

R$_4$ is hydrogen, hydroxy, C$_1$-C$_6$ alkoxy, C$_2$-C$_6$ alkanoyloxy, carboxy, nitro or NHR$_7$, wherein R$_7$ is hydrogen or C$_1$-C$_6$ alkyl;

R$_5$ is hydrogen, C$_1$-C$_6$ alkyl or halogen; and

R$_6$ is hydrogen or C$_1$-C$_6$ alkyl;

n is zero, 1 or 2;

R$_1$ is hydrogen, C$_1$-C$_6$ alkyl or C$_2$-C$_6$ alkanoyl;

R$_2$ is hydrogen, C$_1$-C$_6$ alkyl, halogen, cyano, carboxyl, nitro or —NHR$_7$ in which R$_7$ is as defined above;

R$_3$ is hydrogen, C$_1$-C$_6$ alkyl or C$_2$-C$_6$ alkanoyl;

or a pharmaceutically acceptable salt thereof; and wherein:

(i) when, at the same time, R$_2$ is hydrogen, C$_1$-C$_6$ alkyl, halogen or cyano and R$_3$ is hydrogen, R$_1$ and n being as defined above, then at least one of R$_4$, R$_5$ and R$_6$ is other than hydrogen; and (ii) when n is zero and R$_3$ and R$_6$ are each hydrogen or CH$_3$, then at least one of R$_2$, R$_4$ and R$_5$ is other than hydrogen.

2. A compound of formula (I), according to claim 1, wherein R$_4$ is hydroxy, amino, nitro or carboxy and R$_5$ and R$_6$ are hydrogen;

R$_1$ is hydrogen or C$_1$-C$_6$ alkyl;

n is zero or 1;

R$_2$ is hydrogen, carboxy, amino or nitro;

R$_3$ is hydrogen; and the pharmaceutically acceptable salts thereof.

3. A compound of formula (I), according to claim 1, wherein R$_4$ is hydroxy, amino or carboxy; and R$_5$ and R$_6$ are hydrogen; n is 0 or 1; R$_1$ is hydrogen; R$_2$ is hydrogen, amino or carboxy; R$_3$ is hydrogen; and the pharmaceutically acceptable salts thereof.

4. A compound selected from the group consisting of the following which, when appropriate, may be either Z- or E-diastereoisomers or Z,E-mixtures of said diastereoisomers:

5-hydroxy-3-[(3'-indolyl)methylene]-2-oxindole;
3-[(5'-carboxy-3'-indolyl)methylene]-2-oxindole;
3-[(5'-amino-3'-indolyl)methylene]-2-oxindole;
5-carboxy-3-[(3'-indolyl)methylene]-2-oxindole;
5-amino-3-[(3'-indolyl)methylene]-2-oxindole;
5-hydroxy-3-[(5'-hydroxy-3'-indolyl)methylene]-2-oxindole;
5-hydroxy-3-[(7'-hydroxy-3'-indolyl)methylene]-2-oxindole;
5-amino-3-[(5'-hydroxy-3'-indolyl)methylene]-2-oxindole;
5-hydroxy-3-[(5'-amino-3'-indolyl)methylene]-2-oxindole;
5-carboxy-3-[(5'-hydroxy-3'-indolyl)methylene]-2-oxindole;
5-hydroxy-3-[(5'-carboxy-3'-indolyl)methylene]-2-oxindole;
5-amino-3-[(7'-hydroxy-3'-indolyl)methylene]-2-oxindole;
5-carboxy-3-[(7'-hydroxy-3'-indolyl)methylene]-2-oxindole;
5-methoxy-3-[(5'-methoxy-3'-indolyl)-methylene]-2-oxindole;
5-acetoxy-3-[(5'-acetoxy-3'-indolyl)methylene]-2-oxindole;
3-[(5'-carboxy-3'-indolyl)methylene]-2-oxindole;
3-[(5'-amino-3'-indolyl)methylene]-2-oxindole;
3-[(5'-nitro-3'-indolyl)methylene]-2-oxindole;

and, if the case, the pharmaceutically acceptable salts thereof.

5. A pharmaceutical composition comprising a suitable carrier and/or diluent and, as an active principle, a compound of formula (I) according to claim 1 or a pharmaceutically acceptable salt thereof.

6. A pharmaceutical composition comprising a suitable carrier and/or diluent and, as an active principle, a compound selected from 3-[(1'-methyl-3'-indolyl)methylen]-2-oxindole, 3-[(3'-indolyl)methylen]-1-methyl-2-oxindole and the pharmaceutically acceptable salts thereof, the compound or salt being either the Z- or E-diastereoisomer or a Z/E mixture of diastereoisomers.

7. A method of treating a patient in need of treatment with a tyrosine kinase inhibitor, the method comprising administering thereto a therapeutically effective amount of a compound selected from the compounds of formula (I) and salts thereof, as claimed in claim 1, and the compounds and salts defined in claim 6.

* * * * *